United States Patent [19]

Meltz et al.

[11] Patent Number: 4,482,247

[45] Date of Patent: Nov. 13, 1984

[54] FORWARD SCATTERING LASER PARTICULATE SENSOR

[75] Inventors: Gerald Meltz, Avon; Leon A. Newman, South Windsor; James R. Dunphy, Manchester; Martin C. Foster, Plantsville, all of Conn.

[73] Assignee: United Technologies Corporation, Hartford, Conn.

[21] Appl. No.: 512,311

[22] Filed: Jul. 8, 1983

Related U.S. Application Data

[63] Continuation of Ser. No. 376,861, May 10, 1982, abandoned.

[51] Int. Cl.³ ............................................. G01N 21/00
[52] U.S. Cl. ..................................................... 356/343
[58] Field of Search ............... 356/338, 341, 343, 438, 356/339, 336, 342, 340

[56] References Cited

U.S. PATENT DOCUMENTS

| | | | |
|---|---|---|---|
| 1,969,626 | 8/1934 | Simon et al. | 356/438 |
| 3,310,680 | 3/1967 | Hasegawa | 356/341 |
| 3,662,176 | 5/1972 | Kamentsky et al. | 250/218 |
| 3,666,359 | 5/1972 | Lee | 356/71 |
| 3,713,743 | 1/1973 | Simms | 356/338 |
| 3,743,430 | 7/1973 | Riggs | 356/438 |
| 3,785,735 | 1/1974 | Friedland et al. | 356/39 |
| 4,017,186 | 4/1977 | Shofner et al. | 356/342 |
| 4,099,875 | 7/1978 | McMahon et al. | 250/574 X |
| 4,175,865 | 11/1979 | Horvath et al. | 356/338 |
| 4,249,244 | 2/1981 | Shofner et al. | 356/339 |
| 4,284,412 | 8/1981 | Hansen et al. | 356/39 X |

*Primary Examiner*—Bruce Y. Arnold
*Attorney, Agent, or Firm*—Richard P. Lange; Robert P. Sabath

[57] ABSTRACT

A sensor employs a laser to obtain a collimated light beam for transmission across the gas effluent of a catalytic cracking process. Particulate matter entrained in the gas flow forward scatters light energy to a collecting aperture which, in turn focuses the scattered light on a first photodetector. A second photodetector receives directly transmitted light energy. A ratio between the output signals of the two photodetectors is derived and presented to a threshold level detector. If the magnitude of the scatter exceeds a predetermined level it is concluded that a catalyst load dump has occurred. The optical system is carefully selected to ensure that only light energy scattered from a sample volume within the entrained gas flow reaches the first photodetector. This is important because it prevents particulate matter on the surfaces of the transparent windows from affecting the operating of the sensor.

5 Claims, 5 Drawing Figures

FIG.5
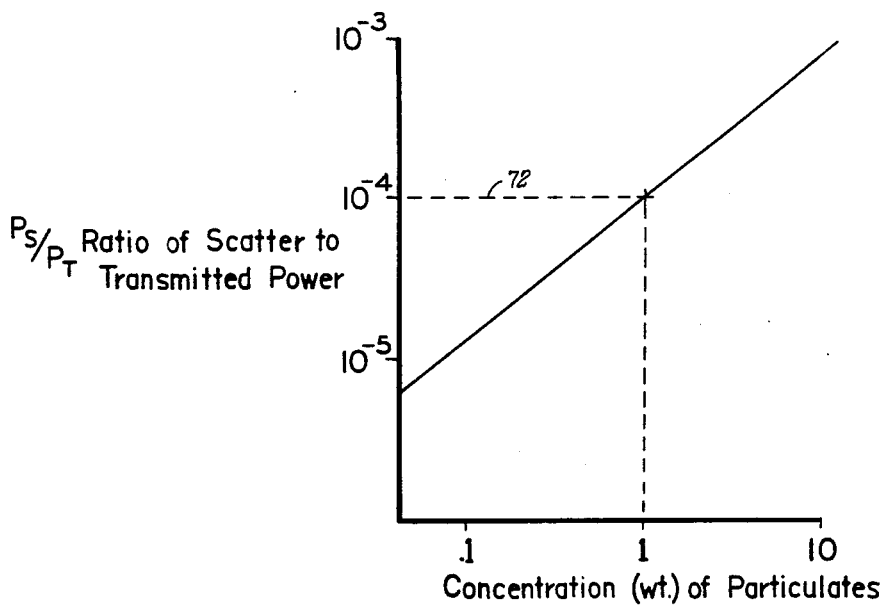
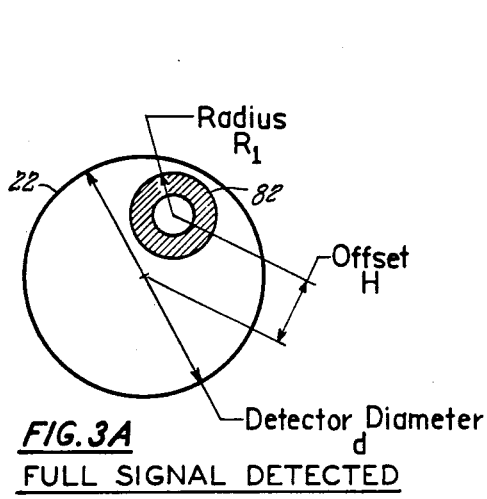
FIG.3A
FULL SIGNAL DETECTED
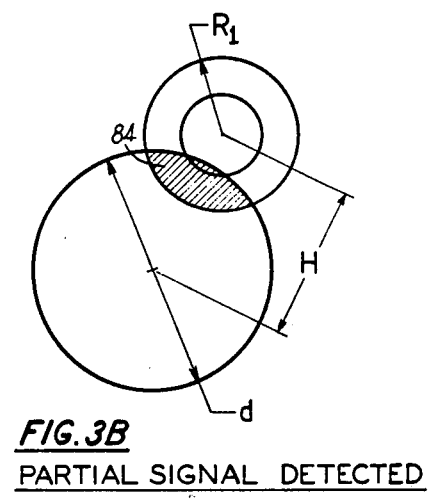
FIG.3B
PARTIAL SIGNAL DETECTED

FORWARD SCATTERING LASER PARTICULATE SENSOR

This is a continuation application of application Ser. No. 376,861, filed May 10, 1982, now abandoned.

DESCRIPTION

1. Technical Field

This invention relates to an optical sensor for detecting an undesirable level of particulates entrained in a gas and, more particularly, to a real-time laser particulate sensor which is well suited for monitoring the effluent of a catalytic cracking process to instantaneously identify an undesirable level of catalyst particles which can damage the turbine blades of an energy recovery device.

2. Background Art

A fluid cracking process is often employed with heavy petroleum fraction in which the heavy hydrocarbon material is heated to a high temperature and brought in contact with catalyst particles. After a period of exposure to the catalysts the heavier hydrocarbons are reduced to lower molecular weight hydrocarbon. During the process it is often necessary to recycle the catalyst particles to remove nonvolatile carbonaceous material which reduces the effectiveness of the catalysts. During the regeneration process the carbonaceous material or coke is removed so that the regenerated catalysts can be returned for use in the cracking process. To conserve energy, the hot gases resulting from the burning of coke is often passed through a heat recovery system.

A major problem in the use of such a power recovery system is that a catalyst load dump can occur. When a catalyst dump occurs, the whole fluidized catalyst bed is generally lost and an enormous amount of the catalyst, a siliceous material, is forced through the turbine blades of the energy recovery system. In some situation, a bypass might be employed to protect the energy recovery system by switching the gas flow from the turbine blades of heat recovery system before damage can take place. A more complete description of the catalytic cracking process together with an energy recovery system utilizing a bypass to protect the energy recovery system is contained in U.S. patent application Ser. No. 06/094,140 filed Nov. 14, 1979 now abandoned.

A key item in providing suitable protection for the waste energy recovery system is the sensor which is employed to detect when a catalyst dump has occurred so that the valves controlling the bypass loop can be quickly triggered. However, it is important for the sensor to distinguish between smoke, dirty sensor windows, and other items which would give a false alarm that would trigger the bypass loop.

One type of particulate sensor is disclosed in U.S. Pat. No. 3,873,206 issued to W. Wilcock for "Method for Determining a Specific Characteristic of Fluid Suspended particles" issued on Mar. 25, 1975. The sensor includes a laser which is positioned in an opening at one side of a stack through which the particulate-laden gas flows. At the opposite side of the pipe a first and second lens are positioned to receive light scattered by the particulates passing through the coherent light beam. The scattered light is focused on a photodetector and produces an output signal which is proportional to the light flux falling on the detector. One problem with this sensor is that it is not particularly well suited for large diameter pipes. To use this sensor with a large diameter pipe means that the collecting aperture for the primary lens must be quite large. Large diameter lenses are undesirable because they are expensive and the large surface area of such lenses are difficult to keep clean. Even though a pressurized airstream might be employed to attempt to keep the surface of the lens and any windows clear, the larger the diameter of the lens, the more difficult it is to keep the surface free of particulate matter. Still another disadvantage of the lens system described in this patent is that it is sensitive to scattering from particulates deposited on the window surfaces. This is because the scattered light is imaged in the Fraunhofer plane of the collecting lens. Another problem with a large aperture lens is that such lenses are subject to aberrations which tend to reduce the accuracy of the collection process. Large collecting lenses also mean that in order to position the photodetector at the focal plane of the lens, the photodetector is going to be a significant distance away from the sidewall of a large diameter pipe, this makes the physical size of the sensor rather cumbersome in addition to making it more difficult to align the system components.

DISCLOSURE OF INVENTION

It is an object of the present invention to provide a real-time forward scattering laser particulate sensor which is particularly well suited to detecting undesirable levels of particulates, such as would be associated with a catalyst dump in a catalytic cracking process, flowing through a large diameter pipe.

An especially significant feature of the forward scattering particulate sensor according to the present invention is that the lens system is so designed that the sensor only responds to particulates in a well defined sample volume within the interior of the pipe. Although the response from this sample volume is somewhat asymmetric, by the careful selection of the lens and relative positioning of the components, the sample volume can be completely contained within the dimensions of a large diameter gas carrying pipe.

Another feature of particular importance of the real-time forward scattering laser particulate sensor, according to the present invention, is that the lens system and photodetectors are so located and sized that the sensor responds only to particulate matter passing through a sample volume within the interior of the pipe and not to any particulate matter on the windows through which the light energy passes.

Still another feature of the real-time forward scattering laser particulate sensor according to the present invention is that the ratio of direct light to forward scattered light is measured at the output end so that any variation in intensity of the incoming light source can be compensated for.

Another feature of the real-time forward scattering laser particulate sensor according to the present invention is that the object window through which forward scattered light passes can have a relatively small diameter with respect to the diameter of the pipe so that keeping the surface free of particulate matter is simplified.

According to yet another feature of the real-time forward scattering laser particulate sensor of the present invention is that it rapidly detects an undesirable level of catalyst particles which can damage the turbine blades of an energy recovery device but yet can distinguish such potentially damaging particles from smoke, source intensity variations, and other nondamaging conditions which could provide a false alarm signal.

The foregoing and other objects, features and advantages of the present invention will become more apparent from the following description of preferred embodiments and accompanying drawings.

BRIEF DESCRIPTION OF DRAWINGS

FIG. 3 is a drawing showing the relationship between the images on the first photodetector of light scattered from particulates scattered from portions of the sample volume shown in FIG. 2;

FIG. 5 is a graph depicting the response curve for the forward scattering laser particulate sensor.

BEST MODE FOR CARRYING OUT THE INVENTION

Figure 1:
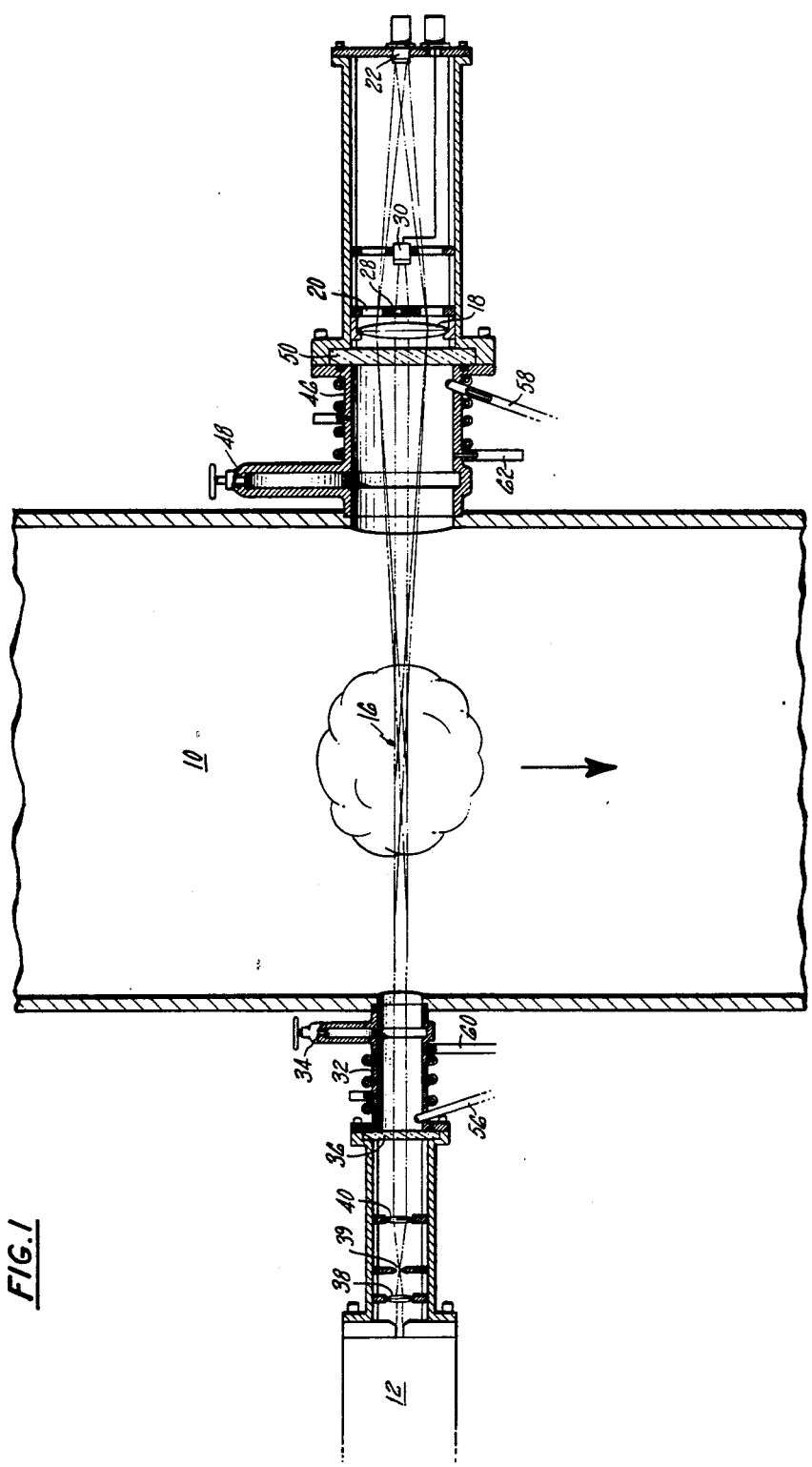
FIG. 1 is a cross-sectional view depicting one embodiment of the forward scattering laser particulate sensor attached to a pipe or duct through which particle-laden gas flows.

Referring initially to FIG. 1, there is seen one embodiment of a real-time forward scattering laser particulate sensor according to the present invention for detecting an undesirably high level of particulate matter entrained in the gas flowing through a pipe 10. The sensor includes a laser 12, such as a 5 mw helium neon laser, which is mounted normal to the sidewall of the pipe 10 and presents a narrow collimated beam of light energy in a direction that is generally normal to the flow of the gas through the pipe 10. Any particulate matter which is entrained in the gas and which passes through a well defined sample volume 16 causes a forward scattering of light energy from the collimated beam. An annular portion of this scattered light energy is collected by a primary lens 18 and is focused through a spatial filter 20, such as an annular stop, onto a first photodetector 22. Directly transmitted, or nonscattered, light energy is collected by a secondary lens 28 which is positioned to focus light onto a second photodetector 30.

Because the gas in the pipe 10 is normally at both a high pressure and a high temperature, it is desirable to isolate the components of the sensor from these severe conditions. Accordingly, mountings 32 and 46, such as a cylindrical section of pipe, are fixedly attached to, and extend radially outward from, opposite sides of the sidewall of the pipe 10. A gate valve 34 is normally provided in the mounting 32 so that a transparent window 36, located at the outward end, can be isolated from the pressure gas in the pipe 10. A beam expander consisting of a condenser lens 38, an aperture 39, and collimating lens 40 would normally be provided to both collimate and increase the diameter of the light beam from the laser 12. It sould be understood that a collimating lens 40 is not essential in every instance. In a similar manner, at the opposite side of the pipe 10, a gate valve 48 is provided in the mounting 46 to allow isolation of a transparent window 50 and the light collection system from the hot, high pressure gas. The length and shape of each mounting 32 and 46 would typically be selected to provide sufficient temperature gradient for cool operation at the outward ends. If necessary, additional heat sinks such as coils 52 and 54 could be positioned on the mounts 32 and 46, respectively, and a coolant circulated therethrough to further increase the temperature gradient between the system components and the high temperature gas.

In the preferred embodiment, a tube 56 and a tube 58 would be provided and attached to the mountings 32 and 46, respectively, for directing purge gas to the surfaces of the windows. There may be one or more ports, which together allow the introduction of the purge gas, such as oil-free air or nitrogen, that flows across each window surface. This keeps the surfaces of the windows clean and prevents particulates from depositing on the surfaces of the windows which would otherwise interfere with light transmission through the windows.

A tube 60 and a tube 62 may also be provided on each mountings 32 and 46 to vent the space closed by the valves 34 and 48. Each tube bleeds or vents the high pressure gas when the valve is in the closed position so that the window can be changed or otherwise serviced.

Figure 2:
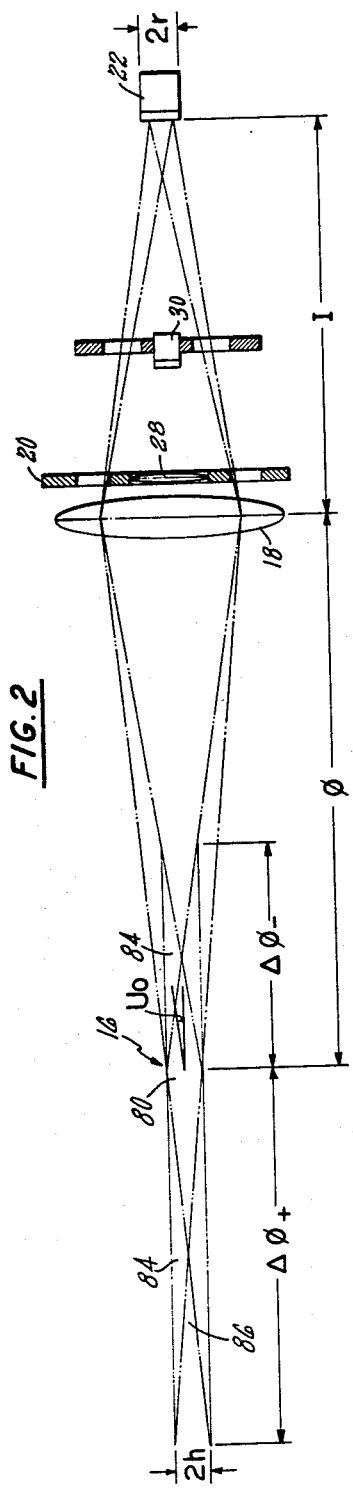
FIG. 2 is an enlarged, and simplified, view of the optical system employed in the present invention.

Referring to FIG. 2 in conjunction with FIG. 3, the effect of light scattered in the sample volume 16 will now be described with respect to its impact on the surface of the detector 22. The area 80 of the sample volume 16 (FIG. 2) is essentially shaped as two conical areas connected at their base, the base being at a distance $\phi$ from the lens 18. Light energy scattered from any point in the portion 80 of the sample volume 16 will be focused by the object lens 18 on the surface of the first photodetector 22. For example, note the annular area 82 (FIG. 3(a)) on the photodetector 22 which illustrates the image of light scattered from a point in the central portion 80 of the sample volume 16. From other portions of the sample volume 16 scattered light also reaches the detector 22. For example, light scattered from the portion 84 of the sample volume 16 (this being adjacent to the volume 80), also reaches the surface of the photodetector 22; however, only a portion of this light energy in fact reaches the photodetector 22. Finally, particulate matter which does not pass through either the volume 80 or the portion 84 of the sample volume 16, would not scatter light along an axis such that it would be received by the object lens 18, admitted by the spatial filter 20 and fall upon the photodetector 22.

One feature of the optical system employed with the present invention is that it selectively defines a sample volume 16 within the interior of the large pipe 10 from which light energy scattered by particles reaches the first photodetector 22. In other words, the first photodetector 22 only responds to light scattered by particles passing through the sample volume 16 and does not respond to light scattered by particulate matter outside of this sample volume. This is especially significant because both the window 36 and the window 50 in operation tend to accumulate some particulates on their surfaces but these particulates do not scatter light energy such that it impinges the first photodetector 22. This is best understood by reference to FIG. 2 in addition to FIG. 1, equation (1) with subsequent discussion hereinafter. The illustration of FIG. 2 is an enlarged, and simplified, view showing the relationship between the sample volume 16, the primary objective lens 18, the filter 20, and the first photodetector 22. Given the nominal object distance $\phi$, from the lens, there will be no scattered light energy reaching the detector 22 for objects further away than $\phi + \Delta\phi_+$ or closer than $\phi - \Delta\phi_-$. The extent of the sample volume, $\Delta\phi_+ + \Delta\phi_-$, is related to the parameters of the optical collection system by the following equation:

$$\Delta\phi_+ = \frac{\frac{hI}{2} + r\phi}{Iu_0 - r} \quad (1)$$

$$\Delta\phi_- = \frac{\frac{hI}{2} + r\phi}{Iu_0 + r}$$

where:
h is the illumination beam radius,
I is the image distance,
r is the detector radius,
$u_0$ (radians) is the half-field of the obscuration.

The foregoing calculations assume that the small angle approximation is valid, i.e., $U_o = \tan U_o$, and that the obscuration is located at the principal plane of the lens. These calculations are valid in the present case where the spatial filter 20 is located in close proximity to the lens 18 since its actual separation from the principal plane is a small fraction of the effective focal length of the lens 18. For angles which are not small, $\tan U_o$ should be substituted for $U_o$.

At this point, it might be helpful to consider some of the design parameters of a particulate sensor according to the principles of this invention. As mentioned, the sensor must be capable of detecting the sudden onset of an abnormally high level of catalyst, downstream of a cyclone separator, in the inlet pipe which feeds the power recovery expander. The inner diameter of this pipe is typically four to six feet in size. For purposes of illustration, assume that the sample volume is to be centered in a four-foot pipe, say at about 60 cm from the windows. From equation (1), it is seen that the size of the sample volume is determined by the beam radius h and the inner numerical aperture $u_0$ of the collecting solid angle $\Omega$. With the beam radius $h = 1$ mm and $u_0 = 1°$, typical values for a commercial size installation, $\Delta\phi_+ = 9.6$ cm and $\Delta\phi_- = 7.8$ cm. Referring to FIG. 2, it is seen that scattering objects farther away than $\phi + \Delta\phi_+$, or nearer than $\phi - \Delta\phi_-$ (where $\phi$ is the nominal center of the sample volume along the beam, in this case 60 cm) will not scatter light energy to the optical signal at the primary detector 22. In other words, scattered light from particles outside this region, which includes the locations of the windows 36 and 50, will not fall on the first detector 22. The length 1 of the effective sample volume is approximately $4/9(\Delta\phi_+ + \Delta\phi_-)$ since signals from particles in some parts of the cylindrical volume defined by the beam and the region contained between $\phi + \Delta\phi_+$ and $\phi - \Delta\phi_-$ are only partially detected. For the parameters given in this example $1 \approx 8$ cm.

The characteristics of the primary objective lens 18 which collects the scattering radiation in the solid angle $\Omega$ are determined by the detector size $2r$, and the nominal location of the center of the sample volume $\phi$. If I is the location of the image of the beam cross section at the center of the sample volume (FIG. 2), then from the lens formulas:

$$1/I + 1/\phi = 1/f \quad (2)$$

Where f is the focal length of the primary lens, and $$r/h = I/\phi \quad (3)$$

It is assumed in the latter equation, that the first detector 22 is just matched to the image of the sample volume cross section. By combining these two equations, one obtains the required focal length:

$$f = \frac{\phi}{\frac{h}{r} + 1} \quad (4)$$

If the first detector 22 has a diameter of 0.5 mm it will require a 120 mm focal length primary lens to obtain the expected reduction in background scattering and the specified sample volume. The f number of the lens is determined by the outer numerical aperture $u_1$ of the solid angle $\Omega$ and $\phi$, with $u_1 = 2°$ and $\phi = 60$ cm, f number $\leq 2.8$.

It should be understood that the spatial filter 20 need not be located at the principal plane of the lens 18, but could be located in either the object space or image space. Then the above equations must be appropriately modified to take into account the location and size of the equivalent entrance and exit pupils of the resulting optical system. For this situation, the maximum lens aperture as well as the size and location of the obscuration with respect to the principal plane of the lens serve to define the sample volume.

Proceeding with this example, assume that under normal conditions 40 lbs/hr of catalyst flows through the cyclone separator upstream of the expander inlet and into the pipe 10 containing the laser particulate sensor. Moreover, as is often the case, the size distribution of the particulates is log-normally distributed by mass (or volume). When the distribution by mass (or volume) is log-normal then the fractional concentration by size will also be log-normal.

The ratio R of the optical power $P_s$, scattered into the solid angle $\Omega$ by the particles in the sample volume, to the directly transmitted power $P_t$ is a measure of the particulate mass loading in the flue gas. If the solid angle $\Omega$ is conical and contained between the polar angles $\theta - \Delta\theta/2$ and $\theta + \Delta\theta/2$, then $$R \equiv \frac{P_s}{P_t} = Nl\overline{\sigma_\Omega} \quad (5)$$

where
N is the particle concentration,
l is the effective length of the cylindrical sample volume, and
$\sigma_\Omega$ is the cross section for forward scattering into the solid angle $\Omega$ averaged over the particle distribution.

This quantity can be computed from the Mie scattering formula by those skilled in this art. If most of the particles are in the size range 1-20 micron and $\Delta\theta \leq \theta < \lambda/2\pi a_{min}$, then $$\overline{\sigma_\Omega} \approx 2\pi^3/\lambda^2 \int_{a\,min}^{a\,max} a^4 n(a) da \quad (6)$$

where
a is the particle radius,
$\lambda$ is the optical wavelength, and
n(a) is the fractional distribution by number.

It follows that R is proportional to the product of the mass (or volume) concentration and the mass (or volume) mean size. This is easily seen by noting that $a^3 n$-

(a)da is the fractional volume (or mass) of particles with radii between a and a+da; hence $$R \propto \rho \bar{d}_v \quad (7)$$

where
- $\rho$ is the particulate density in the flow, and
- $\bar{d}_v$ is the volume (or mass) mean diameter.

Simply stated, the sensor response R is an increasing function of the mass loading and the mean volume diameter. Both of these quantities would be expected to increase when the catalyst bed is upset.

Figure 4:
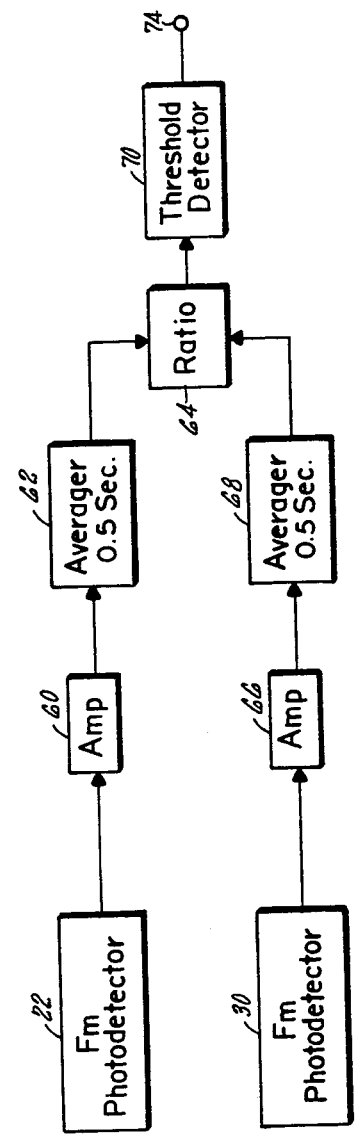
FIG. 4 is a drawing of a simple electrical circuit for processing the output signals from the photodetectors of FIG. 1.

Referring now to FIG. 4, there is seen one embodiment, in block diagram form, of a processing technique for driving signal output from the first photodetector 22 and the second photodetector 30 so as to provide an alarm indication of an undesirably high level of particulate matter flowing through the pipe 10. The output of the first photodetector 22 is presented through a preamplifier 60 to a signal averager 62, typically a low-pass filter. The signal averager 62 provides an output signal which is proportional to the average received intensity of light flux by the first photodetector 22 over a predetermined period of time, normally within the range of about 0.1 to 1 s. The output from the signal averager 62 is a signal which is proportional to the average of the received light flux over a predetermined period of time, normally 0.1 to 1 s. The output from the signal averager 68 is presented to a second input of the ratio detector 64. The output from the ratio detector 64 is then a signal which represents the ratio of the scattered light flux to the transmitted light flux and thus provides a clear indication of the amount of particulate matter within the sample volume 16.

Referring next to FIG. 5, this graph shows a typical response curve for a forward scattering laser particulate sensor according to the present invention for various concentrations of particulate matter flowing through the pipe 10. An alarm signal would be provided by a threshold detector 70 which is connected to receive the output from the ratio detector 64. A predetermined level of particulate matter would be identified as acceptable, such as that represented by level 72 (FIG. 5), and concentrations of particulate matter below this level would not provide an alarm indication. However, if the concentration of particulates exceeded the level 72, an alarm signal at the output 74 of the threshold detector 70 would indicate the excessive concentration of particulates.

As will be appreciated by those of ordinary skill, the simplified signal processing techniques just described for the output of the photodetectors 22 and 30 is only one example. Where the particulate sensor is used to check for a catalyst dump in a fluid cracking process as described earlier, such plants typically employ complex computer control systems which continuously monitor numerous physical conditions throughout the plant. In such a case, the output from the particulate sensor might then be one of many conditions monitored by the control system using a complicated algorithm.

Although this invention has been shown and described with respect to a preferred embodiment, it will be understood by those skilled in this art that various changes in form and detail thereof may be made without departing from the spirit and scope of the claimed invention.

We claim:

1. A sensor for monitoring the level of particulate passing through a sample volume in a gas flow, comprising:
    a light source positioned to direct a beam a light through said sample volume;
    a lens system including a first lens means positioned to collect light scattered from said sample volume;
    a first photo detector means positioned in the image plane of said sample volume to receive light focused thereon by said first lens means from said sample volume for providing a first detector output signal proportional thereto; and
    a spatial filter means, located within said beam of light and having an annular aperture whose inner and outer radii are sized to define limits of said sample volume, said spatial filter means including a second lens means positioned within a central aperture of the spatial filter means;
    second detector means positioned to receive light from said second lens means for providing a second detector output signal proportional thereto such that the ratio between said first detector output signal and said second detector output signal indicates the particulate level in said sample volume.

2. A sensor according to claim 1, wherein said sample volume is aligned with a pair of windows that are located on opposite sides of a pipe, and wherein said light source is positioned on one side of said pipe and said lens system and said first photodetector are positioned on the opposite side of said pipe.

3. A sensor according to claim 2, further comprising a cylindrical mounting means attached to and extending radially outward from opposite sides of said pipe, each of said mounting means opening at its inward end to the interior of a pipe through which said gas flows, and each of said mounting means having a mounting at its outward end of said transparent windows.

4. A sensor according to claim 3, wherein one of said cylindrical means is smaller in diameter than the other cylindrical mounting means, and wherein the smaller of said cylindrical mounting means is adapted to position said light source so that said beam of light passes through the interior of said pipe.

5. A sensor according to claim 3, wherein each of said cylindrical mounting means includes a gate valve positioned adjacent the sidewall of said pipe so that each of said cylindrical mounting means can be isolated from said gas flow.

* * * * *